United States Patent
Fujii et al.

(10) Patent No.: US 10,028,655 B2
(45) Date of Patent: Jul. 24, 2018

(54) OPHTHALMOLOGIC IMAGING APPARATUS AND OPTICAL UNIT ATTACHABLE TO THE SAME

(71) Applicant: KABUSHIKI KAISHA TOPCON, Itabashi-ku (JP)

(72) Inventors: Kouta Fujii, Toda (JP); Kenji Miyashita, Okegawa (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 14/625,884

(22) Filed: Feb. 19, 2015

(65) Prior Publication Data

US 2015/0245765 A1    Sep. 3, 2015

(30) Foreign Application Priority Data

Feb. 28, 2014    (JP) .................................. 2014-038867

(51) Int. Cl.
*A61B 3/14*    (2006.01)
*A61B 3/10*    (2006.01)
(Continued)

(52) U.S. Cl.
CPC ............ *A61B 3/102* (2013.01); *A61B 3/0091* (2013.01); *A61B 3/117* (2013.01); *A61B 3/12* (2013.01); *A61B 3/14* (2013.01); *G02B 27/141* (2013.01)

(58) Field of Classification Search
CPC ........... A61B 3/103; A61B 3/14; A61B 3/113; A61B 3/1225; A61B 3/1015
(Continued)

(56) References Cited

U.S. PATENT DOCUMENTS 6,377,349 B1    4/2002   Fercher
2003/0234908 A1*  12/2003   Kushida .................. A61B 3/14
                                              351/206
(Continued)

FOREIGN PATENT DOCUMENTS

EP    2 347 701 A1    7/2011
EP    2 786 698 A1    10/2014
(Continued)

OTHER PUBLICATIONS

Office Action dated Jul. 23, 2015 in United Kingdom Patent Application No. GB1503045.5.
(Continued)

*Primary Examiner* — Dawayne A Pinkney
(74) *Attorney, Agent, or Firm* — Oblon, McClelland, Maier & Neustadt, L.L.P.

(57) ABSTRACT

An optical system of an ophthalmologic imaging apparatus of embodiment splits light from a first light source into measurement light and reference light and detects interference light of returned light of measurement light from an eye and reference light. An image forming part forms an image based on detection result from the optical system. The optical unit includes a lens and joining member. The lens is locatable in an optical path of measurement light and used for changing a focus position of measurement light from a first site of the eye to second site. The joining member joins an optical path from a second light source to the optical path of measurement light. The optical unit converges light from the second light source having been guided into the optical path of measurement light by the joining member on an eye fundus via the lens.

15 Claims, 6 Drawing Sheets

(51) Int. Cl.
*A61B 3/00* (2006.01)
*A61B 3/117* (2006.01)
*A61B 3/12* (2006.01)
*G02B 27/14* (2006.01)

(58) Field of Classification Search
USPC ........ 351/206, 211, 221, 200, 204, 210, 246
See application file for complete search history.

(56) References Cited

U.S. PATENT DOCUMENTS

| | | | |
|---|---|---|---|
| 2005/0007551 A1* | 1/2005 | Wakil | A61B 3/107 351/205 |
| 2006/0100528 A1 | 5/2006 | Chan et al. | |
| 2007/0242222 A1 | 10/2007 | Iwanaga et al. | |
| 2011/0176111 A1 | 7/2011 | Taki et al. | |
| 2011/0228218 A1 | 9/2011 | Hauger et al. | |
| 2012/0140238 A1* | 6/2012 | Horn | A61B 3/102 356/479 |
| 2013/0258282 A1* | 10/2013 | Goto | A61B 3/1005 351/206 |
| 2013/0258286 A1* | 10/2013 | Iwase | A61B 3/0041 351/208 |
| 2014/0300863 A1 | 10/2014 | Fukuma et al. | |
| 2014/0300864 A1 | 10/2014 | Fukuma et al. | |
| 2014/0300866 A1 | 10/2014 | Fukuma et al. | |
| 2014/0320809 A1 | 10/2014 | Fukuma et al. | |
| 2014/0320810 A1 | 10/2014 | Fukuma et al. | |

FOREIGN PATENT DOCUMENTS

| | | |
|---|---|---|
| JP | 63-164938 A | 7/1988 |
| JP | 6-237901 A | 8/1994 |
| JP | 09-276232 A | 10/1997 |
| JP | 10-192244 A | 7/1998 |
| JP | 10-272104 A | 10/1998 |
| JP | H 11-225970 A | 8/1999 |
| JP | 11-325849 A | 11/1999 |
| JP | 2002-139421 A | 5/2002 |
| JP | 2004-180707 A | 7/2004 |
| JP | 2006-153838 A | 6/2006 |
| JP | 2007-024677 A | 2/2007 |
| JP | 2007-275160 A | 10/2007 |
| JP | 2008-073099 A | 4/2008 |
| JP | 2008-259544 A | 10/2008 |
| JP | 2009-011381 A | 1/2009 |
| JP | 2011-50439 A | 3/2011 |
| JP | 2011-147609 A | 8/2011 |
| JP | 2012-223435 A | 11/2012 |
| JP | 2013-153796 A | 8/2013 |

OTHER PUBLICATIONS

German Office Action dated Sep. 13, 2016, issued in German Patent Application No. 10 2015 203 443.7.
An Invitation to Attend an Oral Hearing dated Oct. 30. 2017, issued in German Patent Application No. 102015203443.7 (with English translation).
Japanese Office Action dated Jan. 9, 2018, issued in Japanese Patent Application No. 2016-150251 (with English translation).

* cited by examiner

OPHTHALMOLOGIC IMAGING APPARATUS AND OPTICAL UNIT ATTACHABLE TO THE SAME

TECHNICAL FIELD

The present invention relates to an ophthalmologic imaging apparatus for acquiring images of an eye by means of optical coherence tomography (OCT) and an optical unit attachable to the same.

BACKGROUND TECHNOLOGY

In recent years, OCT that forms images expressing surface and internal morphologies of an object by using light beam from laser light source etc. has attracted attention. OCT is noninvasive to human bodies unlike X-ray CT and is therefore expected to be utilized in medical and biological fields in particular. For example, apparatuses that form images of fundus, cornea etc. are in a practical stage in ophthalmology.

An apparatus disclosed in Patent Document 1 uses a technique so-called "Fourier Domain OCT." Specifically, the apparatus irradiates low-coherence light beam to an object, superposes reflected light thereof and reference light to generate interference light, acquires spectral intensity distribution of the interference light and executes Fourier transform on it, thereby imaging morphology of the object along a depth direction (z-direction). Further, the apparatus is provided with a galvano mirror for scanning light beam (measurement light) in one direction (x-direction) perpendicular to the z-direction and forms an image of a desired measurement target region of the object. An image formed by this apparatus is a two-dimensional cross-sectional image in the depth direction (z-direction) along the scanning direction (x-direction) of the light beam. The technique of this type is also called Spectral Domain.

Patent Document 2 discloses a technique of scanning measurement light in horizontal and vertical directions (x-direction and y-direction) to form multiple two-dimensional cross-sectional images along the horizontal direction and of acquiring and imaging three-dimensional cross-sectional information of a measured area based on the cross-sectional images. examples of such three-dimensional imaging include a method of arranging and displaying cross-sectional images along the vertical direction (referred to as stack data etc.), a method of executing rendering on volume data (voxel data) based on stack data to form a three-dimensional image.

Patent Documents 3 and 4 disclose other types of OCT. Patent Document 3 describes an OCT apparatus that images morphology of an object by scanning wavelength of light irradiated to an object (wavelength sweeping), detecting interference light obtained by superposing reflected lights of respective wavelengths on reference light to acquire spectral intensity distribution and executing Fourier transform on it. Such an OCT is called Swept Source type. The Swept Source type is a kind of the Fourier Domain type.

Patent Document 4 describes an OCT apparatus that irradiates light having a certain beam diameter to an object and analyzes components of interference light obtained by superposing reflected light thereof and reference light, thereby forming an image of the object in a cross-section orthogonal to travelling direction of the light. Such an OCT apparatus is called full-field type or en-face type.

Patent Document 5 discloses an application of OCT to ophthalmology. Before OCT was applied, retinal cameras, slit lamp microscopes, scanning laser ophthalmoscopes (SLO) etc. were used for observing an eye (see Patent Documents 6, 7 and 8 for example). A retinal camera photographs a fundus by projecting illumination light on an eye and receiving reflected light from the fundus. A slit lamp microscope obtains a cross-sectional image of a cornea by cutting off light section of the cornea by using slit light. An SLO images morphology of retinal surface by scanning a fundus with laser light and detecting reflected light with a highly sensitive imaging element such as a photomultiplier.

As described above, OCT is superior relative to retinal cameras etc. in that high-definition image may be obtained, further in that cross-sectional image and three-dimensional image may be obtained, etc.

Thus, ophthalmologic imaging apparatuses using OCT may be used for observation of various sites of an eye and is capable of acquiring high-definition images; therefore, OCT has been applied to diagnoses of various ophthalmologic disorders. Now, ophthalmologic imaging apparatuses capable of performing OCT measurement of both fundus and anterior eye part are sometimes used for observing various sites of eyes. An Attachment (adopter or optical unit) for changing focus position of measurement light from fundus to anterior eye part is selectively applied to such an ophthalmologic imaging apparatus (see Patent Document 9). This attachment includes a lens having predetermined refractive power.

PRIOR ART DOCUMENTS

Patent Documents

[Patent Document 1] Japanese Laid-open Patent Publication No. H11-325849
[Patent Document 2] Japanese Laid-open Patent Publication No. 2002-139421
[Patent Document 3] Japanese Laid-open Patent Publication No. 2007-24677
[Patent Document 4] Japanese Laid-open Patent Publication No. 2006-153838
[Patent Document 5] Japanese Laid-open Patent Publication No. 2008-73099
[Patent Document 6] Japanese Laid-open Patent Publication No. H09-276232
[Patent Document 7] Japanese Laid-open Patent Publication No. 2008-259544
[Patent Document 8] Japanese Laid-open Patent Publication No. 2009-11381
[Patent Document 9] Japanese Laid-open Patent Publication No. 2012-223435

SUMMARY OF THE INVENTION

Problem that the Invention is to Solve

Fixation is being performed for restraining eye movement during OCT measurement. Fixation is carried out by presenting a fixation target for causing an eye to gaze in a predetermined direction. Many ophthalmologic imaging apparatuses are provided with an optical system for presenting fixation targets (fixation optical system). In ophthalmologic imaging apparatuses capable of performing OCT measurement, part of optical path of measurement light and part of optical path of fixation optical system are common. For example, a common objective lens guides both measurement light and fixation light to an eye.

When an attachment as described above is applied to such an ophthalmologic imaging apparatus, a lens provided in the attachment changes image-formation state of fixation light. In that case, fixation cannot be performed properly. That is, since installation of an attachment shifts image-formation position of fixation light, a subject cannot recognize a fixation target clearly.

A purpose of the present invention is to provide a technology that is capable of performing fixation properly without regard to use/non-use of an attachment.

Means for Solving the Problem

An ophthalmologic imaging apparatus of an embodiment includes: an optical system that splits light from a first light source into measurement light and reference light and detects interference light of returned light of the measurement light from an eye and the reference light; an image forming part that forms an image based on detection result from the optical system; and an optical unit comprising a lens that is locatable in an optical path of the measurement light and used for changing a focus position of the measurement light from a first site of the eye to a second site and a joining member that joins an optical path from a second light source to the optical path of the measurement light, wherein the optical unit converges light from the second light source having been guided into the optical path of the measurement light by the joining member on a fundus of the eye via the lens.

Effect of the Invention

According to the present invention, it is possible to perform fixation properly without regard to use/non-use of an attachment.

MODES FOR CARRYING OUT THE INVENTION

Examples of embodiments of an opthalmological imaging apparatus according to the present invention will be described in detail with reference to the drawings. The ophthalmologic imaging apparatus according to an embodiment forms cross-sectional images and three-dimensional images of eye fundus by using OCT. In the present description, images obtained by OCT are sometimes referred to as OCT images. Further, a measurement operation for forming OCT images is sometimes referred to as OCT measurement. Contents described in the documents cited in this description may be applied to the following embodiments.

In the following embodiments, configurations in which Fourier Domain OCT is employed will be described in detail. Particularly, ophthalmologic imaging apparatuses according to the embodiments are capable of obtaining both a fundus OCT image with Spectral Domain OCT and a fundus image as the apparatus disclosed in Patent Document 5.

By attaching an attachment (optical unit) to this opthalmological imaging apparatus for fundus imaging, its usage is changed to anterior-eye-part imaging. Note that it is possible to change usage of an opthalmological imaging apparatus originally for anterior-eye-part imaging to fundus imaging by attaching an attachment (optical unit) to it. Imaging target sites are not limited to fundus and anterior eye part and may be any sites of an eye such as vitreous body or crystalline lens. Further, a configuration may be applied in which attachments (optical units) are prepared according to imaging target sites, respectively, and these are selectively attached. It is possible to automatically select use/non-use of attachments (optical units) and/or select an attachment to be used. These selections may be executed based on photography modes applied in the past, names of diseases, etc., for example.

Configurations according to the present invention may be applied to an ophthalmologic imaging apparatus of any type other than Spectral Domain such as Swept Source OCT. Further, although a combination of an OCT apparatus and retinal camera is described in the following embodiments, it is possible to combine an OCT apparatus having configurations of the present embodiment with any fundus imaging apparatus other than retinal camera such as an SLO, slit lamp microscope, ophthalmologic operation microscope, etc. Further, Configurations according to the embodiments may be installed in a single-function OCT apparatus.

First Embodiment

[Configurations]

Figure 1:
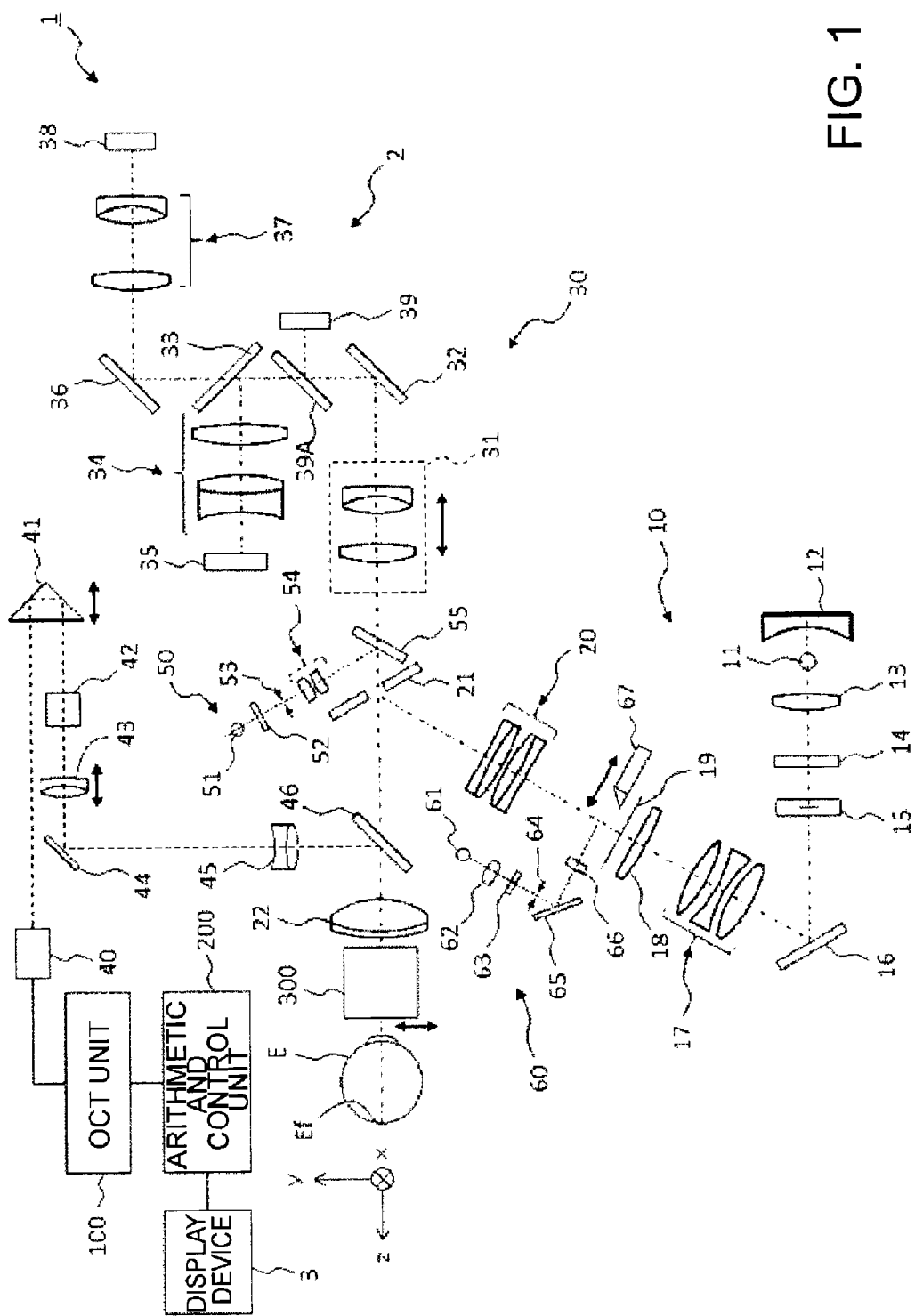
FIG. 1 is a schematic diagram illustrating an example of a configuration of an ophthalmologic imaging apparatus according to an embodiment.
Figure 2:
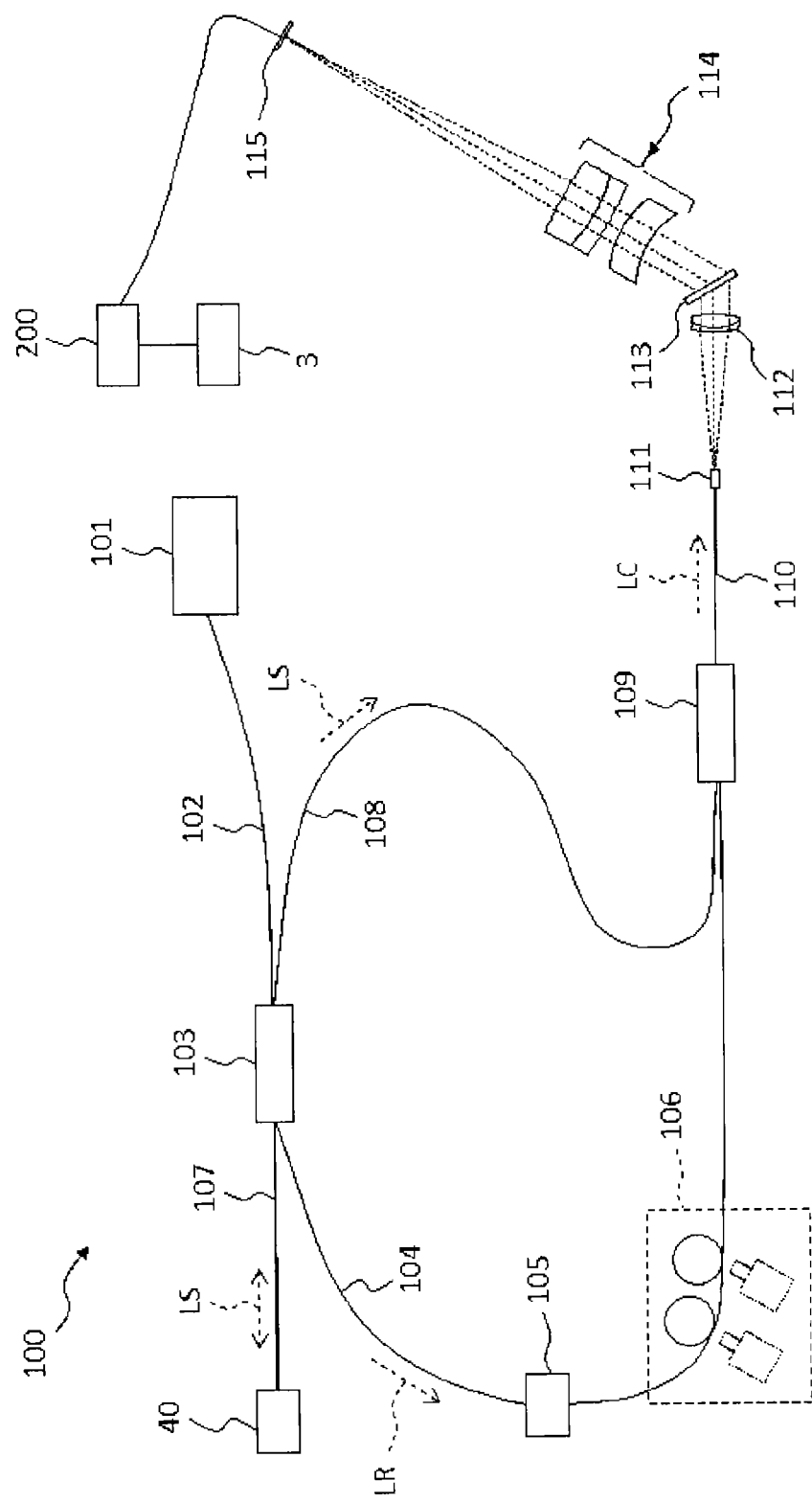
FIG. 2 is a schematic diagram illustrating an example of a configuration of an ophthalmologic imaging apparatus according to an embodiment.

As shown in FIG. 1 and FIG. 2, an ophthalmologic imaging apparatus 1 includes a retinal camera unit 2, an OCT unit 100, an arithmetic and control unit 200 and an optical unit 300 as an attachment. The retinal camera unit 2 has optical systems almost the same as a conventional retinal camera. The OCT unit 100 is provided with optical systems for obtaining OCT images of eye fundus. The arithmetic and control unit 200 is provided with a computer that executes various arithmetic processing, control processing, etc. It is possible to insert/remove the optical unit 300 into/from an optical path toward an eye E. The optical unit 300 is removed from the optical path in the case of fundus OCT measurement and located in the optical path in the case of anterior-eye-part OCT measurement.

[Retinal Camera Unit]

The retinal camera unit 2 shown in FIG. 1 is provided with an optical system for acquiring two-dimensional images (fundus images) representing surface morphology of a fundus Ef of the eye E. Fundus images include observation images, photographed images, etc. An observation image is a monochromatic moving image formed at a predetermined frame rate using near-infrared light, for example. A photographed image may be a color image captured by flashing visible light or a monochromatic still image captured by using near-infrared light or visible light as illumination light, for example. The retinal camera unit 2 may also be capable of capturing other types of images such as a fluorescein angiography image, indocyanine green angiography image and an autofluorescent image.

The retinal camera unit 2 is provided with a chin rest and forehead placement for supporting a subject's face. Moreover, the retinal camera unit 2 is provided with an illumination optical system 10 and imaging optical system 30. The illumination optical system 10 irradiates illumination light to the fundus Ef. The imaging optical system 30 guides fundus reflected light of the illumination light to imaging devices (CCD image sensors 35, and 38 (sometimes referred to simply as CCD)). Moreover, the imaging optical system 30 guides measurement light input from the OCT unit 100 to the fundus Ef and guides the measurement light returned from the fundus Ef (returned light of the measurement light from the fundus Ef) to the OCT unit 100.

An observation light source 11 of the illumination optical system 10 includes a halogen lamp, for example. Light (observation illumination light) output from the observation light source 11 is reflected by a reflection mirror 12 with a curved reflection surface, and becomes near-infrared after passing through a visible cut filter 14 via a condenser lens 13. Further, the observation illumination light is once converged near an imaging light source 15, reflected by a mirror 16, and passes through relay lenses 17 and 18, a diaphragm 19 and a relay lens 20. Then, the observation illumination light is reflected on the peripheral part (the surrounding region of an aperture part) of an aperture mirror 21, transmitted through a dichroic mirror 46, and refracted by an objective lens 22, thereby illuminating the fundus Ef. LED (Light Emitting Diode) may be used as the observation light source.

Fundus reflection light of the observation illumination light is refracted by the objective lens 22, transmitted through the dichroic mirror 46, passes through the aperture part formed in the center region of the aperture mirror 21, transmitted through a dichroic mirror 55, travels through a focusing lens 31, and reflected by a mirror 32. Further, the fundus reflection light is transmitted through a half-mirror 39A, refracted by reflected by a dichroic mirror 33, and forms an image on the light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display device 3. When the imaging optical system is focused on the anterior eye part, an observation image of the anterior eye part of the eye E is displayed.

The imaging light source 15 includes a xenon lamp, for example. The light (imaging illumination light) output from the imaging light source 15 is irradiated to the fundus Ef via the same route as that of the observation illumination light. The fundus reflection light of the imaging illumination light is guided to the dichroic mirror 33 via the same route as that of the observation illumination light, transmitted through the dichroic mirror 33, reflected by a mirror 36, and forms an image on the light receiving surface of the CCD image sensor 38 by a condenser lens 37. An image (photographed image) based on the fundus reflection light detected by the CCD image sensor 38 is displayed on the display device 3. The display device 3 for displaying the observation image and the display device 3 for displaying the photographed image may be the same or different. Further, when similar photographing is carried out by illuminating the eye E with infrared light, infrared photographed image is displayed. Moreover, LED may be used as the imaging light source.

An LCD (Liquid Crystal Display) 39 displays fixation targets, targets for measuring visual acuity etc. A fixation target is a visual target for fixating the eye E used for fundus photography, OCT measurement, etc.

Part of light output from the LCD 39 is reflected by the half-mirror 39A, reflected by the mirror 32, passes through the focusing lens 31 and dichroic mirror 55, passes through the aperture part of the aperture mirror 21, passes through the dichroic mirror 46, refracted by the objective lens 22 and projected onto the fundus Ef.

By changing display position of fixation target on the screen of the LCD 39, fixation position of the eye E may be changed. Examples of fixation positions of the eye E include position for acquiring images centered at macula of the fundus Ef, position for acquiring images centered at optic papilla, position for acquiring images centered at fundus center located between macula and optic papilla, etc. as in conventional retinal cameras. Display position of fixation target may be arbitrarily changed.

The retinal camera unit 2 is provided with an alignment optical system 50 and focus optical system 60 similarly to conventional retinal cameras. The alignment optical system 50 generates target (alignment target) for matching position of the optical system with the eye E (alignment). The focus optical system 60 generates target (split target) for focusing on the fundus Ef.

Light output from an LED 51 of the alignment optical system 50 (alignment light) passes through diaphragms 52 and 53 and a relay lens 54, is reflected by the dichroic mirror 55, passes through the aperture part of the aperture mirror 21, is transmitted through the dichroic mirror 46, and is projected onto cornea of the eye E by the objective lens 22.

Cornea reflection light of the alignment light passes through the objective lens 22, the dichroic mirror 46 and the aperture part, part of the cornea reflection light is transmitted through the dichroic mirror 55, passes through the focusing lens 31, reflected by the mirror 32, transmitted through the half-mirror 39A, reflected by the dichroic mirror 33, and projected onto light receiving surface of the CCD image sensor 35 by the condenser lens 34. An image (alignment target) captured by the CCD image sensor 35 is displayed on the display device 3 together with observation image. The user may conduct alignment operation in the same way as conventional retinal cameras. Further, alignment may be performed in a way in which the arithmetic and control unit 200 analyzes position of the alignment target and moves the optical system (automatic alignment).

When performing focus adjustment, reflection surface of a reflection rod 67 is positioned at a slanted position in the optical path of the illumination optical system 10. Light output from an LED 61 of the focus optical system 60 (focus light) passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Further, the focus light passes through the relay lens 20, is reflected at the aperture mirror 21, is transmitted through the dichroic mirror 46, is refracted by the objective lens 22, and is projected onto the fundus Ef.

Fundus reflection light of the focus light passes through the same route as the cornea reflection light of the alignment light and is detected by the CCD image sensor 35. An image (split target) captured by the CCD image sensor 35 is displayed on the display device 3 together with observation image. The arithmetic and control unit 200 analyzes position of the split target and moves the focusing lens 31 and the focus optical system 60 to perform focusing as in the conventional technology (automatic focusing). Further, focusing may be performed manually while visually recognizing split target.

The dichroic mirror 46 splits OCT optical path from fundus photography optical path. The dichroic mirror 46 reflects light of wavelength band for OCT and transmits light for fundus photography. The OCT optical path is provided with, from the OCT unit 100 in order, a collimator lens unit 40, optical path length changing part 41, galvano scanner 42, focusing lens 43, mirror 44 and relay lens 45.

The optical path length changing part 41 may be moved in a direction indicated by the arrow in FIG. 1, thereby changing length of the OCT optical path. This change of optical path length may be used for correction of optical path length in accordance with axial length of the eye E and for adjustment of interference state. The optical path length changing part 41 may include a corner cube and a mechanism that moves the corner cube, for example.

The galvano scanner 42 changes travelling direction of light (measurement light LS) travelling along the OCT optical path. Thereby, the fundus Ef is scanned by the measurement light LS. The galvano scanner 42 may include a galvano mirror for deflecting the measurement light LS in the x-direction, a galvano mirror for deflecting in the y-direction, and a mechanism for independently driving them. Accordingly, the measurement light LS may be deflected in arbitrary direction on the xy-plane.

[OCT Unit]

A configuration example of the OCT unit 100 is explained with reference to FIG. 2. The OCT unit 100 is provided with an optical system for obtaining OCT images of the fundus Ef. The optical system includes configuration similar to conventional Spectral Domain OCT. Specifically, the optical system has configuration that splits low-coherence light into measurement light and reference light, superposes the measurement light returned form the fundus Ef and the reference light having traveled through reference optical path to generate interference light, and detects spectral components of the interference light. The result of detection (detection signal) is transmitted to the arithmetic and control unit 200.

In the case of Swept Source OCT, a wavelength-sweeping light source is provided instead of a low-coherence light source while an optical member for spectrally decomposing interference light is not provided. In general, any known technology according to OCT type may be arbitrarily applied to configuration of the OCT unit 100.

A light source unit 101 outputs broadband low-coherence light L0. The low-coherence light L0, for example, includes near-infrared wavelength band (about 800-900 nm) and has coherence length of about tens of micrometer. Instead, it is possible to use near-infrared light of invisible wavelength band for human eyes as the low-coherence light L0 such as infrared light with center wavelength of about 1040-1060 nm.

The light source unit 101 may include light output device such as SLD (super luminescent diode), LED, SOA (Semiconductor Optical Amplifier), etc.

The low-coherence light L0 output from the light source unit 101 is guided to a fiber coupler 103 by an optical fiber 102 and split into the measurement light LS and the reference light LR.

The reference light LR is guided to an optical attenuator 105 by an optical fiber 104. Through any known technology, the optical attenuator 105 is under the control of the arithmetic and control unit 200 and automatically adjusts light amount (light intensity) of the reference light LR guided in the optical fiber 104. The reference light LR whose light amount has been adjusted by the optical attenuator 105 is guided to a polarization controller 106 by the optical fiber 104. The polarization controller 106 applies stress to the loop-form optical fiber 104 from outside to adjust polarization state of the reference light LR guided in the optical fiber 104, for example. Configuration of the polarization controller 106 is not limited to this and arbitrary known technology may be applied to it. The reference light LR whose polarization state has been adjusted by the polarization controller 106 is guided to a fiber coupler 109.

The measurement light LS generated by the fiber coupler 103 is guided by the optical fiber 107 and converted into a parallel light flux by the collimator lens unit 40. Further, the measurement light LS travels through the optical path length changing part 41, galvano scanner 42, focusing lens 43, mirror 44 and relay lens 45, and reaches the dichroic mirror 46. Further, the measurement light LS is reflected by the dichroic mirror 46, refracted by the objective lens 22 and projected to the fundus Ef. The measurement light LS is scattered (and/or reflected) at various depth positions of the fundus Ef. Back-scattered light (returned light) of the measurement light LS from the fundus Ef travels along the same route as the outward way in the opposite direction to the fiber coupler 103, and is reached the fiber coupler 109 through an optical fiber 108.

The fiber coupler 109 superposes the back-scattered light of the measurement light LS and the reference light LR having passed through the optical fiber 104. Interference light LC thus generated is guided by an optical fiber 110 and output from an exit end 111. Further, the interference light LC is converted into a parallel light flux by a collimator lens 112, spectrally divided (spectrally decomposed) by a diffraction grating 113, converged by a condenser lens 114, and projected onto the light receiving surface of a CCD image sensor 115. Although the diffraction grating 113 illustrated in FIG. 2 is of transmission type, any other kind of a spectrally decomposing element (such as reflection type) may be used.

The CCD image sensor 115 is for example a line sensor and detects respective spectral components of the spectrally decomposed interference light LC and converts them into electric charges. The CCD image sensor 115 accumulates such electric charges, generates detection signal and transmits the detection signal to the arithmetic and control unit 200.

Although Michelson-type interferometer is employed in the present embodiment, any type of interferometer such as a Mach-Zehnder-type may be employed as necessary. Instead of CCD image sensor, other types of image sensors such as CMOS (Complementary Metal Oxide Semiconductor) image sensor may be used.

[Arithmetic and Control Unit]

Configuration of the arithmetic and control unit 200 will be described. The arithmetic and control unit 200 analyzes detection signals input from the CCD image sensor 115 to form OCT images of the fundus Ef. Arithmetic processing for that may be the same as conventional Spectral Domain OCT.

The arithmetic and control unit 200 controls each part of the retinal camera unit 2, display device 3 and OCT unit 100. For example, the arithmetic and control unit 200 displays OCT images of the fundus Ef on the display device 3.

As controls for the retinal camera unit 2, the arithmetic and control unit 200 executes controls of the observation light source 101, imaging light source 103, LED's 51 and 61, LCD 39, focusing lenses 31 and 43, reflection rod 67, focus optical system 60, optical path length changing part 41, galvano scanner 42, etc.

Further, as controls for the OCT unit 100, the arithmetic and control unit 200 executes control of the light source unit 101, optical attenuator 105, polarization controller 106, CCD image sensor 115, etc.

The arithmetic and control unit 200 includes a microprocessor, RAM, ROM, hard disk drive, communication interface, etc. as in conventional computers. Storage device such as the hard disk drive stores computer programs for controlling the ophthalmologic imaging apparatus 1. The arithmetic and control unit 200 may be provided with various circuit boards such as circuit boards for forming OCT images. The arithmetic and control unit 200 may be provided with operation devices (input devices) such as a keyboard, mouse, etc. and/or a display device such as LCD etc.

The retinal camera unit 2, display device 3, OCT unit 100 and arithmetic and control unit 200 may be integrally arranged (that is, housed within a single case) or separately arranged in two or more cases.

[Control System]

Figure 3:
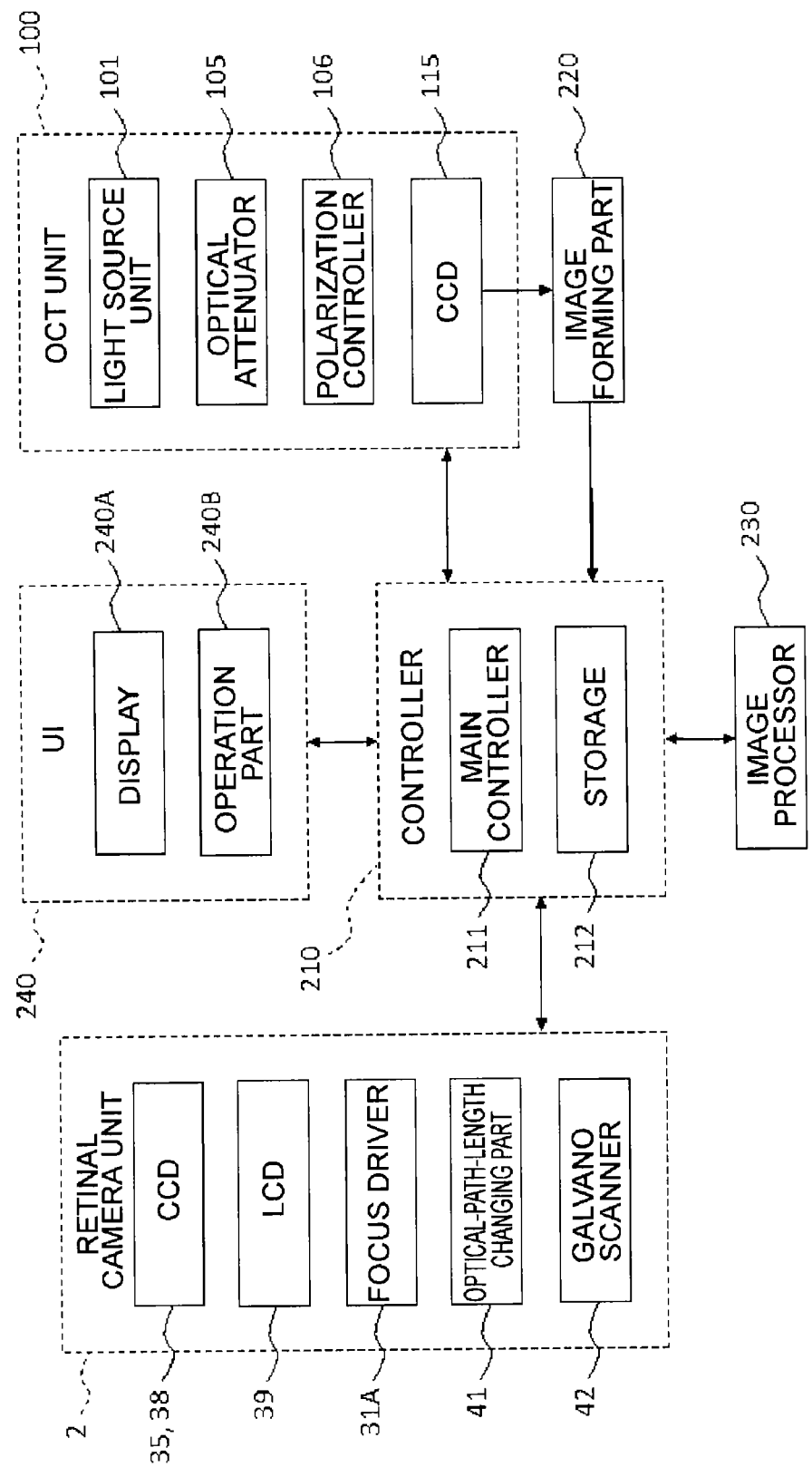
FIG. 3 is a schematic block diagram illustrating an example of a configuration of an ophthalmologic imaging apparatus according to an embodiment.

Configuration of control system of the ophthalmologic imaging apparatus 1 will be described with reference to FIG. 3.

(Controller)

Center of control system of the ophthalmologic imaging apparatus 1 is a controller 210. The controller 210 includes the aforementioned microprocessor, RAM, ROM, hard disk drive, communication interface, etc., for example. The controller 210 is provided with a main controller 211 and storage 212.

(Main Controller)

The main controller 211 performs various kinds of controls described above. In particular, the main controller 211 controls a focus driver 31A, optical path length changing part 41 and galvano scanner 42 of the retinal camera unit 2 as well as the light source unit 101, optical attenuator 105 and polarization controller 106 of the OCT unit 100.

The focus driver 31A moves the focusing lens 31 in the optical-axis direction. Thereby, Focus position of the imaging optical system 30 is changed. The main controller 211 may control an optical system driver (illustration omitted) to move the optical system provided in the retinal camera unit 2 three-dimensionally. This control is used for alignment and tracking. Tracking is an operation for moving the optical system in accordance with eye movement of the eye E. In the case of performing tracking, alignment and focusing are performed in advance. Tracking is a function of moving the optical system so as to follow eye movement in order to maintain suitable positional relationship in which alignment and focusing are matched.

The main controller 211 writes data into the storage 212 and reads out data from the storage 212.

(Storage)

The storage 212 stores various kinds of data. Data stored in the storage 212 may include OCT image data, fundus image data, eye information, etc. The eye information includes information on a subject such as patient ID and name and information on an eye such as left/right eye identification etc. The storage 212 stores various programs and data for operating the ophthalmologic imaging apparatus 1.

(Image Forming Part)

The image forming part 220 forms image data of a cross-sectional image of the fundus Ef based on detection signals from the CCD image sensor 115. This processing includes noise elimination (noise reduction), filtering, FFT (Fast Fourier Transform), etc. similarly to conventional Spectral Domain OCT. in the case of other types of OCT, the image forming part 220 executes known processing according to the type applied.

The image forming part 220 includes circuit boards described above, for example. Note that "image data" and "image" based on the image data may be identified with each other in the description.

(Image Processor)

An image processor 230 executes various kinds of image processing and analysis on images formed by the image forming part 220. For example, the image processor 230 executes various corrections such as brightness correction, dispersion correction of images, etc. The image processor 230 executes various kinds of image processing and analysis on images obtained by the retinal camera unit 2 (fundus images, anterior-eye images, etc.).

The image processor 230 executes known image processing such as interpolation of pixels between cross-sectional images to form three-dimensional image data of the fundus Ef. Three-dimensional image data is image data in which of pixel positions are defined by three-dimensional coordinate system. Examples of three-dimensional image data include image data composed of three-dimensionally arranged voxels. Such image data is referred to as volume data or voxel data. In the case of displaying images based on volume data, the image processor 230 executes rendering (volume rendering, MIP (Maximum Intensity Projection), etc.) on volume data and forms image data of a pseudo three-dimensional image from a preset viewpoint. This pseudo three-dimensional image is displayed on a display device such as a display 240A.

Stack data of multiple cross-sectional images may be formed as three-dimensional image data. Stack data is image data obtained by three-dimensionally arranging multiple cross-sectional images obtained along multiple scanning lines based on positional relation of the scanning lines. In other words, stack data is image data obtained by expressing multiple cross-sectional images defined by originally individual two-dimensional coordinate systems by a single three-dimensional coordinate system (that is, obtained by embedding cross-sectional images into a three-dimensional space).

Such an image processor 230 includes the aforementioned microprocessor, RAM, ROM, hard disk drive, circuit boards, etc., for example. Computer programs for causing the microprocessor to perform above functions are previously stored in storage devices such as the hard disk drive.

(User Interface)

A user interface 240 includes the display 240A and operation part 240B. The display 240A includes a display device of the arithmetic and control unit 200 and/or the display device 3. The operation part 240B includes manipulators of the arithmetic and control unit 200. The operation part 240B may include buttons, keys, etc. provided on the case of the ophthalmologic imaging apparatus 1 or outside thereof. For example, when the retinal camera unit 2 has a case similar to conventional retinal cameras, a joy stick, operation panel, etc. provided on the case may be included in the operation part 240B. The display 240A may include various display devices such as touch panel etc. provided on the case of the retinal camera unit 2.

It is not necessary for the display 240A and operation part 240B to be configured individually. For example, like touch panel, display function and operation function may be integrated. In this case, the operation part 240B includes touch panel and computer programs. Content of operation to the operation part 240B is input into the controller 210 as electrical signals. Operations and/or information input may be performed by using graphical user interface (GUI) displayed on the display 240A and the operation part 240B.

[Optical Unit]

Figure 4:
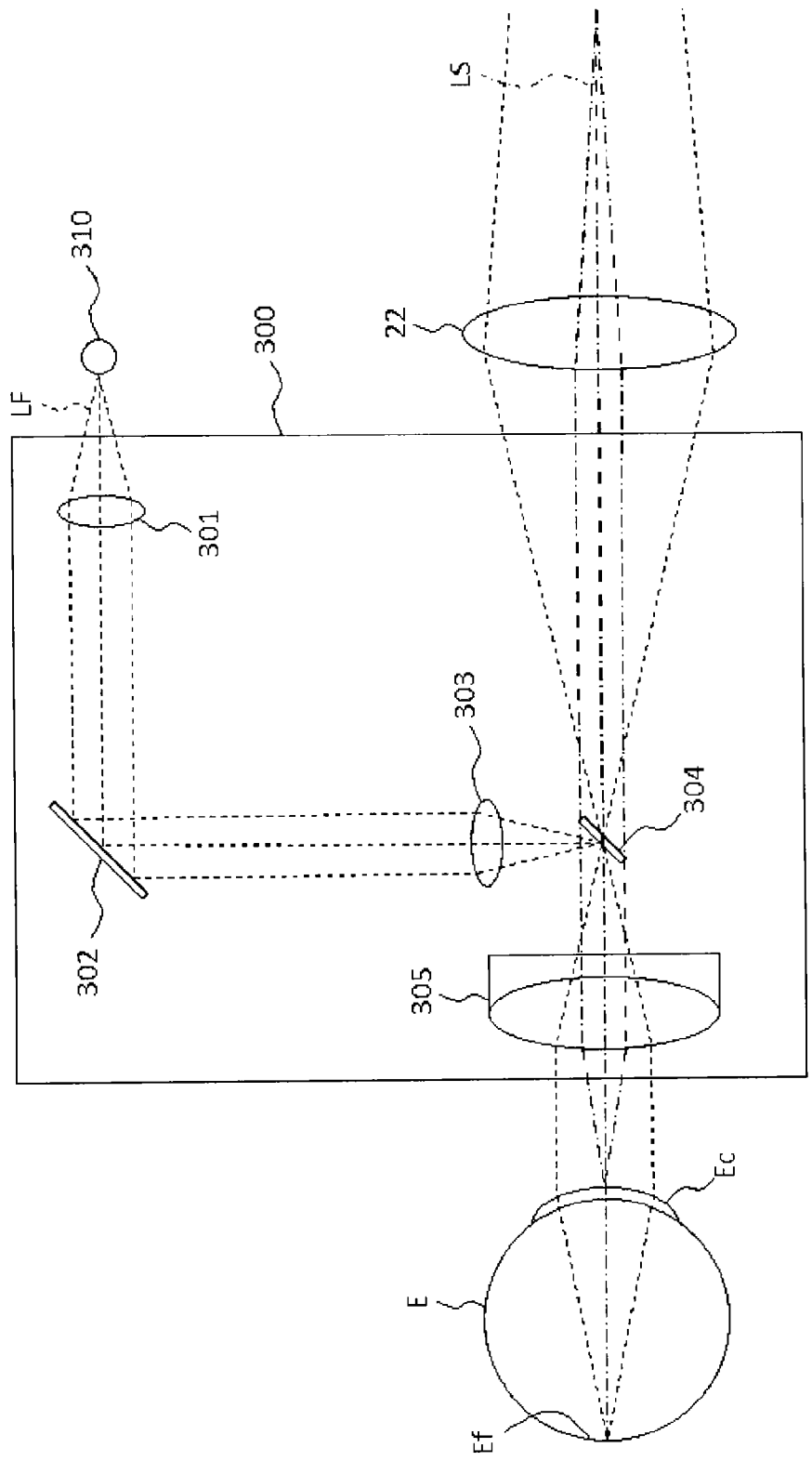
FIG. 4 is a schematic diagram illustrating an example of a configuration of an optical unit according to an embodiment.

Configuration example of the optical unit 300 is illustrated in FIG. 4. The optical unit 300 is positioned in front of the objective lens 22, that is, positioned between the objective lens 22 and the eye E when OCT measurement of the anterior eye part Ea of the eye E is performed. The optical unit 300 includes a lens (objective lens 305) for converging the measurement light LS for OCT measurement on the anterior eye part Ea and an optical system for projecting a fixation target onto the fundus Ef.

As another example, in the case in which an optical unit is attached to an ophthalmologic imaging apparatus for cornea (anterior eye part), this optical system is removed from the optical path in the case of corneal OCT measurement and located in the optical path in the case of fundus OCT measurement. This optical unit includes a lens for converging measurement light on the fundus and an optical system for projecting a fixation target onto the fundus.

In the present example, a light source (fixation light source 310) for generating fixation target is arranged outside the optical unit 300. A fixation light source may be arranged inside an optical unit. In all cases, a fixation light source may be dedicated to fixation or may also be used for other functions. A fixation light source outputs at least visible light, for example.

When a fixation light source is provided outside an optical unit, the fixation light source is used for projecting internal fixation targets in the case of corneal OCT measurement and used as an external fixation light source in the case of fundus OCT measurement, for example. The fixation light source may have arbitrary functions other than external fixation light source such as a function for projecting patterns for measuring corneal shape.

Figure 5:
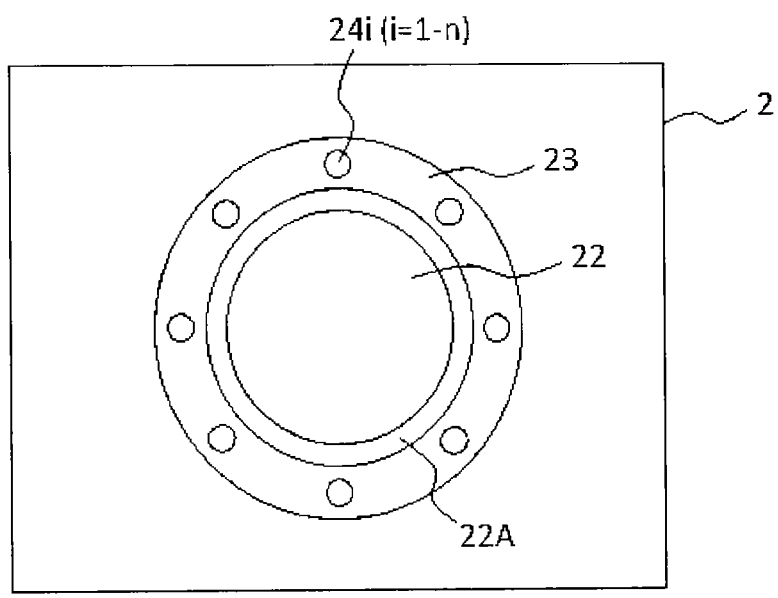
FIG. 5 is a schematic diagram illustrating an example of a configuration of an ophthalmologic imaging apparatus according to an embodiment.

FIG. 5 illustrates an example of the case in which an external fixation light source for performing peripheral fixation in fundus OCT measurement is provided. Peripheral fixation is a kind of fixation for carrying out OCT measurement of peripheral area of fundus. FIG. 5 shows a schematic view of a front face (face on the eye E side) of the retinal camera unit 2 (the case thereof). The objective lens 22 is arranged on the front face of the retinal camera unit 2. The objective lens 22 is housed in a lens-barrel 22A. A light-source holder 23 is provided around the lens-barrel 22A. A plurality of external fixation light sources 24$i$ (i=1 to n) for peripheral fixation are provided in the light-source holder 23. Each external fixation light source 24$i$ is an LED, for example. In the present example, the plurality of external fixation light sources 24$i$ are arranged on a circle centered at the optical axis of the objective lens 22 at equal intervals. The controller 210 controls the fixation light sources 24$i$ (turning on/off, blinking, changing output light amount, changing output wavelength, etc.).

The optical unit 300 is arranged on the front face of the retinal camera unit 2. Light output from any of the fixation light sources 24$i$ (one located at highest position, for example) is used as light output from the fixation light source 310 shown in FIG. 4.

In the case in which a fixation light source is arranged inside an optical unit and the optical unit may be removed from the optical path while being connected to the ophthalmologic imaging apparatus, light from the fixation light source may be guided to the outside of the optical unit by means of light guiding means such as an optical fiber, thereby using this light as other usages (external fixation light source etc.).

An example shown in FIG. 4 is described. The optical unit 300 of the present example includes a relay lens 301, reflection mirror 302, relay lens 303, beam splitter 304 and objective lens 305.

Light output from the fixation light source 310 and entered in the optical unit 300 (fixation light LF) is guided to the relay lens 301. The relay lenses 301 and 303 function as an optical system for relaying an image of the fixation light source 310 to the beam splitter 304. More specifically, the fixation light LF becomes a parallel light flux through the relay lens 301, is reflected by the reflection mirror 302, and converged on a reflection surface of the beam splitter 304 by the relay lens 303.

The beam splitter 304 is arranged at a location conjugate to the fundus Ef, for example. The beam splitter 304 joins optical path of the fixation light LF and optical path of the measurement light LS. The beam splitter 304 is a dichroic mirror that reflects visible light (fixation light LF) and transmits infrared light (measurement light LS), for example. Alternatively, the beam splitter 304 may be a half mirror.

The fixation light LF transmitted the beam splitter 304 is converged (that is, forms an image) on the fundus Ef by the objective lens 305 and eyeball optical system of the eye E. Accordingly, an fixation target based on the fixation light source 310 is projected on the fundus Ef.

On the other hand, the measurement light LS passes through the objective lens 22 of the retinal camera unit 2, passes through the beam splitter 304 of the optical unit 300, and is converged on the cornea Ec by the objective lens 305.

[Effects]

Effects of the ophthalmologic imaging apparatus 1 are explained.

The ophthalmologic imaging apparatus 1 includes an optical system, image forming part and optical unit. The optical system splits light from a first light source (light source unit 101, for example) into measurement light and reference light and detects interference light of returned light of the measurement light from an eye and the reference light. The image forming part (image forming part 220, for example) forms an image based on detection result from the optical system (detection signals generated by the CCD image sensor 115, for example).

The optical unit (optical unit 300, for example) is locatable in an optical path of the measurement light. The optical unit includes a lens that is used for changing a focus position of the measurement light from a first site of the eye to a second site. A combination of the first and second sites is arbitrary. For example, the first site is a fundus and the second site is an anterior eye part (such as cornea). Alternatively, the first site is an anterior eye part (such as cornea) and the second site is a fundus. Further, the optical unit includes a joining member that joins an optical path from a second light source (fixation light source) to the optical path of the measurement light. The joining member may be a beam splitter of any type (dichroic mirror 304, half mirror, etc., for example). The joining member of the optical unit converges light from the second light source having been guided into the optical path of the measurement light on a fundus of the eye via the lens.

According to the ophthalmologic imaging apparatus thus configured, light from the second light source may be converged on the fundus through the optical unit when the optical unit is applied. Therefore, the subject is capable of visually recognizing fixation target clearly even if position of convergence (position of image-formation) of a fixation light flux from an optical system that is a different system from the optical unit is shifted from a retina due to the use of the optical unit. Accordingly, it is possible to perform fixation properly without regard to use/non-use of the optical unit. Note that the second light source may be an LED, flat panel display (such as LCD etc.).

The first light source may output light including infrared light and the second light source may output light including visible light. In this case, the joining member may include a dichroic mirror (dichroic mirror 305, for example).

The second light source may be provided in the optical unit. That is, the optical unit may project fixation target on the fundus based on the light from the second light source provided therein. According to such a configuration, although the second light source is required to be provided in the optical unit, configurations for guiding light from a light source previously provided in the ophthalmologic imaging apparatus to the optical unit are not required.

The second light source may be provided outside the optical unit. That is, the optical unit may project fixation target on the fundus based on the light from the second light source provided thereout. According to such a configuration, it is possible to utilize a light source previously provided in the ophthalmologic imaging apparatus (this light source may have a function other than fixation) as the second light source for projecting fixation target on the fundus when using the optical unit. Accordingly, simplification of configuration of the optical unit may be advanced.

When the second light source is provided outside the optical unit, any of the following configurations may be adopted. Firstly, the optical system may include an objective lens (objective lens 22, for example) and one or more light sources arranged around the objective lens (external fixation light sources 24i, for example). Further, the second light source may include any of the one or more light sources. In such a configuration, any of light sources provided outside the optical unit and provided around the objective lens of the optical system for OCT measurement are used as the second light source for projecting fixation target on the fundus when using the optical unit.

When the opthalmological imaging apparatus includes one or more external fixation light sources (external fixation light sources 24i, for example), the second light source may include any of the one or more external fixation light sources The optical unit may include a relay optical system that relays an image of the second light source to the joining member. According to such a configuration, simplification of configuration of the optical unit may be advanced. In the case of adopting this configuration, the second light source may be a substantial point source of light.

Second Embodiment

The present embodiment describes switching control of means for fixation between use and non-use of an attachment (optical unit). Hereinafter, symbols used in the first embodiment are applied.
[Configuration]
Configuration of optical system of an ophthalmologic apparatus of the present embodiment may be the same as that of the first embodiment (see FIGS. 1, 2 and 5). Further, an optical unit (attachment) may be the same as that of the first embodiment (see FIG. 4).

Figure 6:
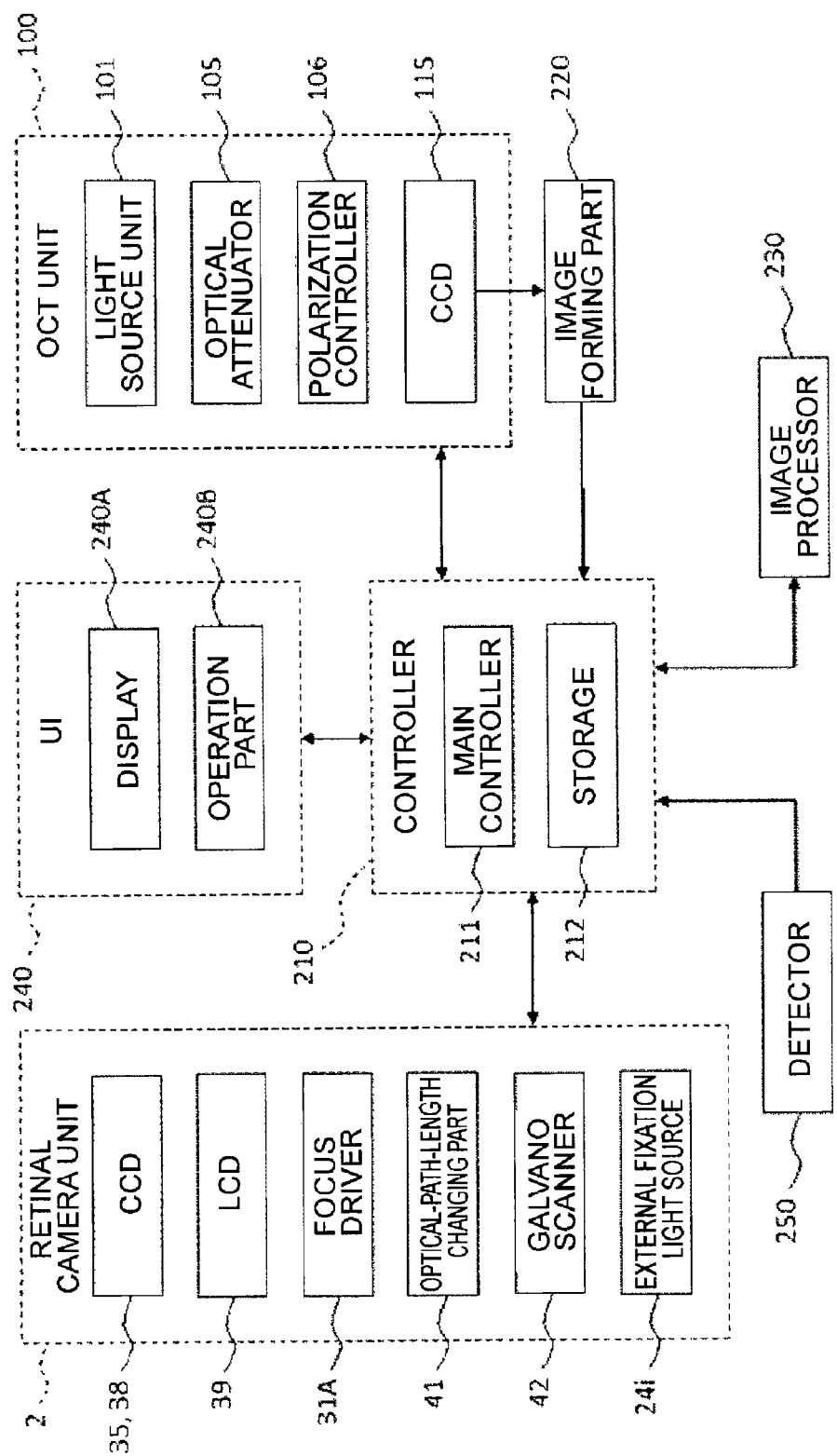
FIG. 6 is a schematic block diagram illustrating an example of a configuration of an ophthalmologic imaging apparatus according to an embodiment.

A control system of the ophthalmologic apparatus of the present embodiment has a configuration illustrated in FIG. 6, for example. Difference from the control system of the first embodiment (FIG. 3) is presence of a detector 250 and clear indication of the external fixation light sources 24i.

The external fixation light sources 24i correspond to fixation light source (second light source) provided outside the optical unit 300. As described in the first embodiment, the fixation light source provided outside the optical unit 300 is not limited to external fixation light source. On the other hand, when fixation light source is provided inside the optical unit 300, the controller 210 controls this fixation light source (turning on/off, blinking, changing output light amount, changing output wavelength, etc.).

The detector 250 detects whether or not the optical unit 300 is located in the optical path of the measurement light LS. The detection means one or both of detection of an event that the optical unit 300 is located in the optical path and detection of an event that the optical unit 300 is not located in the optical path. The detector 250 includes a micro switch, position sensor, etc., for example.

When a micro switch is employed, the micro switch is arranged at a location contacting with the optical unit 300 arranged in the optical path of the measurement light LS, for example. This micro switch is turned on when the optical unit 300 is located in the optical path of the measurement light LS and turned off when it is removed from the optical path. This micro switch inputs signals to the controller 210 when it is "on". The controller 210 recognizes whether or not the optical unit 300 is located in the optical path by presence/absence of such signals.

When a position sensor is employed, the position sensor detects current position of the optical unit 300 and inputs signals indicating detection result to controller 210, for example. The controller 210 recognizes whether or not the optical unit 300 is located in the optical path based on contents of such signals.

As in the first embodiment, a fixation optical system for presenting a fixation target to the eye E is installed in the ophthalmologic apparatus of the present embodiment. This fixation optical system may include the LCD 39. Light output from the LCD 39 is reflected by the half-mirror 39A, reflected by the mirror 32, passes through the focusing lens 31 and dichroic mirror 55, passes through the aperture part of the aperture mirror 21, passes through the dichroic mirror 46, refracted by the objective lens 22 and converged on the fundus Ef. When the optical unit 300 is located in front of the objective lens 22, the subject cannot visually recognize fixation target clearly because the LCD 39 and the cornea Ec are conjugate to each other.

Operations executed by the controller 210 are explained. Upon recognizing that the optical unit 300 is located in the optical path of the measurement light LS, the controller 210 executes control for converging light from the external fixation light source 24i by means of the optical unit 300. This control includes at least turning on the external fixation light source 24i. In the case in which LCD 39 is outputting light at the time of recognizing that the optical unit 300 is located in the optical path of the measurement light LS, the controller 210 turns off the LCD 39.

On the other hand, upon recognizing that the optical unit 300 is not located in the optical path of the measurement light LS, the controller 210 executes control for presenting fixation target by the fixation optical system installed in the ophthalmologic imaging apparatus. This control includes at least control of the LCD 39 to display fixation target. In the case in which the external fixation light source 24i is outputting light at the time of recognizing that the optical unit 300 is not located in the optical path of the measurement light LS, the controller 210 turns off the external fixation light source 24i.

[Effects]

Effects of the ophthalmologic imaging apparatus of the present embodiment are explained.

The ophthalmologic imaging apparatus of the present embodiment provides the same effects as the first embodiment.

In addition, the ophthalmologic imaging apparatus of the present embodiment may execute control for converging light from the second light source (external fixation light source 24i, for example) on the fundus by means of the optical unit (optical unit 300, for example) when the optical unit is used. Therefore, manual operation is not required for switching means for fixation at the time of use of the optical unit (at the time of transferring from fundus OCT measurement to anterior-eye-part OCT measurement, for example).

Further, the ophthalmologic imaging apparatus of the present embodiment may execute control for presenting fixation target by the fixation optical system provided in the ophthalmologic imaging apparatus when the optical unit is not used. Therefore, manual operation is not required for switching means for fixation at the time of non-use of the optical unit (at the time of transferring from anterior-eye-part OCT measurement to fundus OCT measurement, for example).

In this way, according to the ophthalmologic imaging apparatus of the present embodiment, it is possible to improve operability at the time of setting or switching target site of OCT measurement.

Configuration of the detector is not limited to that detecting position or action of the optical unit. For example, the detector may detect use/non-use of the optical system based on information input from outside. Specifically, the detector may recognize use/non-use of the optical system before inserting or removing the optical unit into or from the optical path based on content of examination input by the user (explicit or implicit indication of measurement target site, for example). Alternatively, it is possible to recognize use/non-use of the optical system by referring to electric medical record of a concerned subject (such as content of examination), for example.

<Optical Unit>

The optical units described in the above embodiments are attachable to an ophthalmologic imaging apparatus having OCT function. This ophthalmologic imaging apparatus includes an optical system and image forming part. The optical system splits light from a first light source into measurement light and reference light and detects interference light of returned light of the measurement light from an eye and the reference light. The image forming part forms an image based on detection result from the optical system.

The optical unit is locatable in an optical path of the measurement light. Further, the optical unit includes a lens that is used for changing a focus position of the measurement light from a first site of the eye to a second site and a joining member that joins an optical path from a second light source to the optical path of the measurement light. In addition, the optical unit is configured to converge light from the second light source having been guided into the optical path of the measurement light by the joining member on a fundus of the eye via the lens. The second light source is provided inside or outside the optical unit.

The first light source may output light including infrared light, the second light source may output light including visible light, and the joining member may include a dichroic mirror. The optical unit may include a relay optical system that relays an image of the second light source to the joining member.

According to the optical unit thus configured, it is possible to perform fixation properly without regard to use/non-use of the optical unit.

Modification Examples

Configurations described above are merely illustrations for implementing the present invention. Therefore, it is possible to make arbitrary modification (omission, replacement, addition, etc.) within the scope of the present invention.

In the above embodiments, projecting position of fixation target by the optical unit 300 may be changeable. For example, it is possible to apply a configuration in which projecting position of fixation target is changed by replacing the reflection mirror 302 in the optical unit 300 with a deflecting mirror. The deflecting mirror may be a two-dimensional deflecting mirror such as a dual-axis galvano mirror and operated by receiving control from the controller 210. As another configuration for changing projecting position of fixation target, a mechanism that moves the beam splitter 304 may be provided. This mechanism moves the beam splitter 304 along a normal direction of functioning face of the beam splitter 304 (face having a function joining/splitting optical paths, face having filtering function, etc.). This mechanism is operated by receiving control from the controller 210. According to the present example, since fixation position of the eye E may be changed when performing anterior-eye-part OCT measurement, it is possible to facilitate OCT measurement of arbitrary site of cornea (such as peripheral site).

In the above embodiments, focus adjustment of fixation target projected on the fundus Ef by the optical unit 300 may be performed. For example, focus adjustment of fixation target may be realized by providing a mechanism that moves the relay lens 303 (and/or the reflection mirror 302) in the optical unit 300 along the optical-axis direction. This mechanism is operated by receiving control from the controller 210. As an example of this control, the ophthalmologic imaging apparatus 1 may analyze an image (such as observation image) of the eye E acquired in real time to obtain projection state (focus state) of fixation target, and control the mechanism according to the projection state. Alternatively, the ophthalmologic imaging apparatus 1 may display a real-time image of the fundus Ef on which fixation target is being projected, and control the mechanism according to manual operation performed by the user based on the displayed image. According to the present example, it is possible to present, to the eye E, suitable fixation target whose focus is matched.

The optical units 300 described in the above embodiments are merely example. For example, regarding arrangement of optical elements, the beam splitter 304 is not necessarily arranged at a position of pupil conjugate.

In the above embodiments, optical path length difference between optical paths of measurement light LS and reference light LR is changed by varying position of the optical path length changing part 41; however, a method of changing optical path length difference is not limited to this. For example, it is possible to change optical path length difference by providing a reflection mirror (reference mirror) in optical path of reference light and moving the reference mirror in the advancing direction of the reference light to change the optical path length of the reference light. Further, optical path length difference may be changed by moving the retinal camera unit 2 and/or OCT unit 100 with respect to the eye E to change the optical path length of the measurement light LS. Moreover, in the case in which an object is not a living tissue or the like, it is possible to change optical path length difference by moving the object in the depth direction (z-direction).

Computer programs for implementing the above embodiments can be stored in any kind of recording medium readable by computers. As such recording media, for example, an optical disk, a semiconductor memory, a magneto-optic disk (CD-ROM, DVD-RAM, DVD-ROM, MO, and so on), and a magnetic storage (a hard disk, a Floppy Disk™, ZIP, and so on) can be used.

In addition, it is possible to transmit/receive such programs through networks such as internet, LAN etc.

What is claimed is:

1. An ophthalmologic imaging apparatus comprising:
    an objective lens;
    an optical system that splits light from a first light source into measurement light and reference light and detects interference light of returned light of the measurement light from an eye and the reference light via the objective lens;
    an image forming part that forms an image based on detection result from the optical system;
    a fixation optical system that presents a first fixation target to the eye via the objective lens;
    an optical unit comprising a lens that is locatable in an optical path of the measurement light and used for changing a focus position of the measurement light from a first site of the eye to a second site and a joining member that joins an optical path from a second light source to the optical path of the measurement light, wherein the optical unit converges light from the second light source having been guided into the optical path of the measurement light by the joining member on a fundus of the eye via the lens as a second fixation target; and
    one or more external fixation light sources that are located outside the optical unit and are arranged on a circle centered at an optical axis of the objective lens;
    wherein the optical unit is placed/removed in/from an optical path of the measurement light between the eye and the objective lens;
    the second light source comprises any of the one or more external fixation light sources; and
    the lens is located in an optical path of light from the fixation optical system.

2. The ophthalmologic imaging apparatus of claim 1, wherein the first light source outputs light including infrared light, the second light source outputs light including visible light, and the joining member comprises a dichroic mirror.

3. The ophthalmologic imaging apparatus of claim 1, wherein the optical unit comprises a relay optical system that relays an image of the second light source to the joining member.

4. The ophthalmologic imaging apparatus of claim 1, wherein the first site is the fundus and the second site is an anterior eye part.

5. The ophthalmologic imaging apparatus of claim 1, wherein the first site is an anterior eye part and the second site is the fundus.

6. The ophthalmologic imaging apparatus of claim 1, further comprising:
    a detector that detects whether or not the optical unit is located in the optical path of the measurement light; and
    a controller that executes control for converging the light from the second light source on the fundus of the eye by the optical unit when the detector detects that the optical unit is located in the optical path of the measurement light.

7. The ophthalmologic imaging apparatus of claim 6, wherein the controller executes control for presenting the fixation target by the fixation optical system when the detector detects that the optical unit is not located in the optical path of the measurement light.

8. The ophthalmologic imaging apparatus of claim 4, wherein the optical unit comprises a relay optical system that relays an image of the second light source to the joining member.

9. The ophthalmologic imaging apparatus of claim 5, wherein the optical unit comprises a relay optical system that relays an image of the second light source to the joining member.

10. The ophthalmologic imaging apparatus of claim 4, further comprising:
    a detector that detects whether or not the optical unit is located in the optical path of the measurement light; and
    a controller that executes control for converging the light from the second light source on the fundus of the eye by the optical unit when the detector detects that the optical unit is located in the optical path of the measurement light.

11. The ophthalmologic imaging apparatus of claim 5, further comprising:
    a detector that detects whether or not the optical unit is located in the optical path of the measurement light; and
    a controller that executes control for converging the light from the second light source on the fundus of the eye by the optical unit when the detector detects that the optical unit is located in the optical path of the measurement light.

12. The ophthalmologic imaging apparatus of claim 3, further comprising:
    a detector that detects whether or not the optical unit is located in the optical path of the measurement light; and
    a controller that executes control for converging the light from the second light source on the fundus of the eye by the optical unit when the detector detects that the optical unit is located in the optical path of the measurement light.

13. An optical unit attachable to an ophthalmologic imaging apparatus that comprises an objective lens and an optical system that splits light from a first light source into measurement light and reference light and detects interference light of returned light of the measurement light from an eye and the reference light via the objective lens and an image forming part that forms an image based on detection result from the optical system, wherein the optical unit is placed/removed in/from an optical path of the measurement light between the eye and the objective lens, the ophthalmologic imaging apparatus further comprising a fixation optical system that presents a first fixation target to the eye via the objective lens, and the optical unit comprising:
    a lens that is used for changing a focus position of the measurement light from a first site of the eye to a second site; and a joining member that joins an optical path from a second light source to the optical path of the measurement light, wherein the optical unit converges light from the second light source having been guided into the optical path of the measurement light by the joining member on a fundus of the eye via the lens as a second fixation target;

one or more external fixation light sources that are located outside the optical unit and are arranged on a circle centered at an optical axis of the objective lens;

the second light source comprises any of the one or more external fixation light sources; and the lens is located in an optical path of light from the fixation optical system.

14. The optical unit of claim 13, wherein the first light source outputs light including infrared light, the second light source outputs light including visible light, and the joining member comprises a dichroic mirror.

15. The optical unit of claim 13, further comprising a relay optical system that relays an image of the second light source to the joining member.

* * * * *